(12) United States Patent
Keshi et al.

(10) Patent No.: US 6,660,852 B1
(45) Date of Patent: Dec. 9, 2003

(54) PROBE FOR DIAGNOSING INFECTIOUS DISEASES

(75) Inventors: Hiroyuki Keshi, Osaka (JP); Soji Eda, Kyoto (JP); Hirotsugu Uehara, Takarazuka (JP); Hiroshi Ueyama, Osaka (JP); Akio Matsuhisa, Osaka (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 08/809,254

(22) PCT Filed: Oct. 2, 1995

(86) PCT No.: PCT/JP95/02036
§ 371 (c)(1),
(2), (4) Date: May 16, 1997

(87) PCT Pub. No.: WO96/10647
PCT Pub. Date: Apr. 11, 1996

(30) Foreign Application Priority Data

Sep. 30, 1994 (JP) ............................................. 6/236348

(51) Int. Cl.$^7$ ........................... C12N 15/63; C07H 21/00
(52) U.S. Cl. .................. 536/24.32; 536/23.1; 536/24.3; 435/320.1
(58) Field of Search ............................. 536/24.32, 23.7, 536/24.3, 23.1, 24.33, 24.31; 435/91.2, 252.3, 253.4, 91.1, 89, 69.1, 7.34, 4, 6, 172.1, 243, 885, 7.9, 7.72, 320.1; 935/19, 76, 77, 78

(56) References Cited

FOREIGN PATENT DOCUMENTS

FR     2 687 168 A1     8/1993

OTHER PUBLICATIONS

Boehringer Mannheim Biochemicals, Catalog (1991); pp. 557.*
Diaz et al Gene (1990) 90: 157–162.*

* cited by examiner

*Primary Examiner*—Gary Kunz
*Assistant Examiner*—Robert C. Hayes
(74) *Attorney, Agent, or Firm*—Marshall, Gerstein & Borun LLP

(57) ABSTRACT

A probe derived from bacteria of pneumonia, containing fragments of DNA which *streptococcus pneumoniae* essentially possesses, and useful for detecting and identifying causative bacteria of pneumonia is obtained by completely digesting the DNA with a restriction endonuclease PstI, followed by cloning into a suitable vector.

15 Claims, 2 Drawing Sheets

SEQUENCE LISTING

<160> NUMBER OF SEQ ID NOS: 9

<210> SEQ ID NO 1
<211> LENGTH: 368
<212> TYPE: DNA
<213> ORGANISM: Artificial sequence
<220> FEATURE:
<223> OTHER INFORMATION: Synthetic probe

<400> SEQUENCE: 1

```
ctgcagcttt caaggaacct gtcaagagag ccagtttcaa attgggaaaa aggttctgta      60
aactctcaaa gtgttgctct gcgaggattt ctgttggtac cattagggca gcctgataac     120
ctgctgtcac tgccgcaaac atggccaagc cagcgactac cgttttttcc actccccaca     180
tccccttgta ggagacgatt catgtggtgg tcggacttca tatcagttaa aatttcctgc     240
aaactctttt cctgagcttg ggtcagggca aaaggaagac ttactttaac tgctgtcact     300
tttccctgag accaattcag aaccagacca cttccctgaa ctctatttc agacttgagc      360 atctgcag                                                             368
```

<210> SEQ ID NO 2
<211> LENGTH: 1978
<212> TYPE: DNA
<213> ORGANISM: Artificial sequence
<220> FEATURE:
<223> OTHER INFORMATION: Synthetic probe
<220> FEATURE:
<221> NAME/KEY: misc_feature
<222> LOCATION: (281)
<223> OTHER INFORMATION: N = A or T or G or C

<400> SEQUENCE: 2

```
ctgcaggttc ccctgtattt gctggtttca ttactggttt aatcatggga gatgtgacta      60
ctggtttact tatcggtggt aacttgcaac tgttcgttct tggggttggt accttcggtg     120
gtgcttctcg tatcgacgca acttctggtg cggttcttgc gacagccttc tctgtttcac     180
aaggaattga tgcaccgctt gccattacta caatcgctgt accagtagca gctctcttga     240
cttacttcga cgttcttggt cgtatgacta ctaccttctt ngctcaccgt gtggatgctg     300
caatcgaacg ctttgactat aaggtattga acgcaactac ttgcttggtg cgattcgtgg     360
gctctatctc gtgcccttcc agtcttcttt gcccttgctt ttggtggtgc ctttgtacaa     420
tcagtagtag acttcgttga agcctacaaa tgggttgcat atggcttgac acttgcagga     480
cgtatgcttc caggtcttgg atttgcaatc ttgcttcgtt accttccagt taaacgtaac     540
cttcactacc ttgctatggg atttggtttg acagctatgt tgactgttct ttactcatat     600
gtaacaggtc ttggtggcgc tgttgctggt atcgtaggta ctcttcctgc tgaagttgct     660
```

| | |
|---|---|
| gaaaaaattg gtttcgtgaa caacttcaaa ggtttgtcta tgattggtat ttctatcgta | 720 |
| ggtatttttcc ttgcagtgct tcacttcaaa aatagccaaa aagtagctgt agcagcacct | 780 |
| tctacaccat cagaaagtgg ggaaatcgaa gatgacgaat tctaattaca aacttacaaa | 840 |
| agaagatttt aatcaaatca acaaacgtag cttgtttact ttccaattag gttggaacta | 900 |
| cgaacgtatg caagcttctg gttaccttta catgatcttg cctcagttgc gtaaaatgta | 960 |
| tggtgatgga actcctgaat tgaaagaaat gatgaaagtt catactcaat tcttcaatac | 1020 |
| ttcaccattc ttccatacca ttatcgctgg ttttgacctt gccatggaag aaaaagatgg | 1080 |
| tgtaggttca aaagacgccg ttaacggtat caagacaggt ttgatgggac cattcgctcc | 1140 |
| tcttggggat acaatctttg cttcacttgt acctgctatc atggggtcag tcgcagcaac | 1200 |
| tatggctatc gctggccaac cttgggggat cttcctttgg attgcagttg cagtagcgta | 1260 |
| tgacatcttc cgttggaaac agttggaatt tgcttacaaa gaaggggtta accttatcaa | 1320 |
| caacatgcaa agtaccttga cagctttgat tgacgctgca tctgtacttg gtgtcttcat | 1380 |
| gatgggtgct cttgtagcaa cagtgattaa ctttgaaatt tcttacaagt tgccaatcgg | 1440 |
| tgaaaagatg attgatttcc aagacatctt gaatcaaatc ttcccacgtt gcttccagc | 1500 |
| aatctttact gcctttatct tctggttgct tggtaagaaa ggtatgaact ctactaaagc | 1560 |
| tatcggtatt attatcgtac ttgctttggc tctttctgcc cttggtcact ttgcacttgg | 1620 |
| aatgtaattc cttatgacta aatcattaat tttgtgagcc atggtcgctt ctgtgaggag | 1680 |
| cttagaggta gcacagaaat gattatgggc ccacaagaca acatttacac agtagctctt | 1740 |
| cttccagaag atgggcccaga agaatttact gctaaatttg aagctgttat tggaggattg | 1800 |
| gatgatttcc tagtctttgc ggatcttctc ggtgggacac cttgtaatgt ggtgagtcgc | 1860 |
| ttgatcatgg aaggtcgtga tattgacctt tacgcaggga tgaatcttcc aatggtgatt | 1920 |
| gaatttatca atgcgagcct tacaggcgca gatgcggact acaagagccg tgctgcag | 1978 |

<210> SEQ ID NO 3
<211> LENGTH: 1124
<212> TYPE: DNA
<213> ORGANISM: Artificial sequence
<220> FEATURE:
<223> OTHER INFORMATION: Synthetic probe

<400> SEQUENCE: 3

| | |
|---|---|
| ctgcaggttt tgtcctcaac ctcccaatca aagaaaatat gagaaatctg cgagttaaga | 60 |
| ttgagaaaaa gacgggccta ctatggaata gatggcaaac aatctatgaa aacagaccaa | 120 |
| ttttagctca accccaccgt aaaattaccc attggggtac gacattgaat tccaaggtga | 180 |
| gtgacgatga tgtcttgtaa tctgatggta gaatgacagt tagtttgtct agtttataag | 240 |
| aaagtactac ctgagcttga atagaactca ggtagctctc tatgaaagaa caaaattaat | 300 |
| actcaatgaa aatcaaagag caaactagga aactagccgc agtttgctca aagcactgct | 360 |
| ttgaggttgt agataagact gacgaagtcg tcaccatata taatccaagg cgacgttgac | 420 |
| gtggattgaa gagatttttag aagagtataa acagaaaggt agagcgcgtg ttctaatttg | 480 |
| aacacgagta gaaaactttt ctaaaagcaa aaacgaaagg atgggtaaac tgtattcgct | 540 |
| gaactgaata cggcgactc tcctctaaat caaaattaag aaaggaattg accccaccct | 600 |
| aaaagtagtg ggaaaagat agttggtcta gcgagcatcg ctcactgcgc ccaactccta | 660 |
| ttttcccttc gctttttgat gggtttggta tctttctcaa tataaaatat aaataagaag | 720 |
| atagagcgtg tgttttgatt tgaacacgag cggaaaactc ggaaaataga taatctgact | 780 |

-continued

```
gaaaaatcag gatttctcgt caggttccta attttcagtc gttttcttct cgctctttgt      840
atcataaatt atgtctatcc atattgctgc tcagcagggt gaaattgctg ataaaattct      900
tcttcctggg gatcctcttc gtgctaagtt tattgcggag aatttccttg atgatgctgt      960
ttgttttaac gaagtgcgta acatgtttgg ttacactggt acttacaagg gtcactgtgt     1020
atctgtcatg ggaactggga tgggaatgcc atctatttcg atttatgcgc gtgagttaat     1080
cgtagactac ggtgtgaaga aattgattcg tgtgggaact gcag                      1124
```

<210> SEQ ID NO 4
<211> LENGTH: 5829
<212> TYPE: DNA
<213> ORGANISM: Artificial sequence
<220> FEATURE:
<223> OTHER INFORMATION: Synthetic probe

<400> SEQUENCE: 4

```
ttcatgcacc aatatattat aataatcttc atccaataat aaggctgata aactagcatc       60
ttggtcaaaa tgtaagggaa tttctcggcc gtccttcttt aatgtatatt ctggtaagat      120
actaaatagt tcaatcatag aaggaaactc aggattagtt gttgtaaatc gaaaaagctg      180
cgctttctca tctttcctga cttccttgat actctcccaa ttctaaaaaa tgattcaagg      240
tagtataaaa ttccttattt tttacttcat caatgatgac catatcataa tctttttgttg     300 tgcgactttt aaatccttgc gaatccaata cgatagaggt agcagttccc ccaatcagaa      360
cataatagtt ctgaaaatcc gcaaacgttt cttgaaaaat aactttcgta ttagctggca      420
tcatcttctc ccagatactg taatatcata ttttctagtg cttcactctc ttcctctata      480
cgtgggtcat catcatcttt taaggtcaaa taaagagaaa tcggatctac aaattgttta      540
tcatgattat ttttaaaatc attccaaaac tcagatacaa aaggacgata tttccatatc      600
tctagcatct ttccttttaa aatatgctga gaaagtggca aggataactg attgaatttt      660
ctctgccata tgacatagct agtattttca tccgtttcag ctaaaaaagt tgaatgcgac      720
aaagcataag caccaccata tagaaggtta gaaacagatt ttatctgctt tatatcgcca      780
tctggcaata aaatccgttt tttgatggga ttaaataaac atgacacgga ttttaagaat      840 aattcttttct ttgacaccgt atatgtgtaa agcttatttt gcttgtttaa ccaatataaa     900 gcttttaaaag tcctcaaaca cctataaatt gttgagtttg gaagtccagt gacttgtgaa     960
agcaaatcaa catctactac tttttgacct tttgtcaata aaaaggcaat ccacgttaat     1020
tgttcgctag gtgttaattc cttagggact tcagtatcat tcgcattgag tactagtccc     1080
aatggaggga agaagaggtt tcccttaaag tctacaaacg gaactctagc ttgaagtaat     1140
tgcttttttt cactgtctga taacttcgaa aacaccaaaa caacatccat attggctttt     1200
tcacccatag tgcgagcctg agtaacaaat gaactcaaac tcccccttct cttttctttta    1260 atcaataaaa atgattcctt atgaaaagtc atttgagtat actcaaacct ttttacaaaa     1320
ctgattgata aagtcaaagt cagttcctca atactgacat caacataaaa ggattgaaaa     1380
attgacatta tcttttttgac attcatgttt tttccttatt ctatcatttt tattatattt    1440
tatcattcgg tataataaaa tataagttttt ttgataaaat aaccaaaaac tactcccctat   1500 cccctctcac actaccctac atatcgtttg acatgcgact gatagttcag gaaaacttca     1560
aggagaactt ttctctcatc cactatgcag gacttactat ttcacttcta ctcctatagg     1620
ctcaatttga cactttttctt tttcgaattg ctcatatgcc tcctgaatag tgagttcgat    1680
ttatccaaat ttattttgt ctattttgat gaatacttcc acgaagatag tctgaaaatg      1740
```

```
aatttgcacc aattttcctt ctcttttaa gcatattatt ccagatatga ttgccctctt    1800
gttcagtaat aaattacgct ttaaacgctt caatcagtat atctcctgtt gtcatatgtt    1860
ctaaagaaaa ttcttctaca tatgatttaa catctcttag gttattactt cctaatatcc    1920
cattatgctt tttcgctaag gaaatagaag ccgcttctcc cttaccaata atcttgttac    1980
tatcatgatt tcttgttaaa tctctatata atgcgtattc ttcagttcca atgtctatgc    2040
tcacaatctc agctgaaccc ttagctacca actgatctat cctagatttt aaatggggaa    2100
ttgtaggtat attgatttca tcatacacct cttgtggaat aacaatttta cccgaataga    2160
gcttttctaa aagatgttca gtaccaaccc ataaaaatac tgaaatacaa tctgcatcaa    2220
taaatacacg actagtcaaa cgacaactcc cccctcttca tctagcccat atacaatatc    2280
atatctgaaa gcatctagta acagttcctc atacttccct tgcgaaattc tgctattttc    2340
taaagtgttc agtcaattat atatatacta ataccatttc cttttactt tctgacaaag    2400 gacgatataa acttgtatca tagcctaatc ttgaagctgt ctctataaca ctaatatcca    2460 tattttaat ttcttctgca tcaaggtatc catcattcct caatctatat aacatagctt    2520
tatgactgat accataaaac tgacccaatt ttataatatc ttctacttca agatgagttc    2580
tattggcatt ttctctgatt tcctcaacca tcctatacag tgaaatggga aaattaaaaa    2640
ataagaagca aactgatccg cttttctttc agtttcatct ccttcaccaa tcaagataag    2700
actgactgaa ctcttcttca cctcatcata ataaagatga tacagttcat gtgctaaaga    2760
aaatctttac cttcctaatg gcatgtctga attgactgca atgagactga aatgagttcc    2820
tttataacag accccgctaa tattcttccc gagtccataa ataccagcg tcaaattttc    2880 tatcttttgt accaatttaa aaatatctat cggcgattca ccatcagctc ccaactttt    2940 tctaagattt ggagctttat tacttaaatc cattcgtgat attcctttca cctttttcca    3000
ttttggcaat catgctttga ttcaaagaca aatactcagc aatcttatct tgagtaagat    3060
ttgaagatat tctaagttct tttattcttt ttccaacatc acatacattt atcatataca    3120
tttatcatat tcatttatca tattcataca cctctcataa aaagaatagc acactcttgt    3180
cataattttt taaataaaaa aattatgaca aaacaaggaa gcaatttatt gatgctgctt    3240
aaaaatctaa aattgatgat attaaaccta tttgatgaat tcctatcaaa aatcgtatct    3300
tcaacctcaa aacagtactt aaagctatcc gactcggttt acattgtcaa atttagattt    3360
tatttgagca taacttttcta gtttgctttt tgatttttgt ttaatatagt agcaaaaatt    3420
gaaggaaata tctccacaag aaaacgcata ctattaagct ttttcaagac ctaataatat    3480
gcgctgttct gatttgaaag acattccatt attattttac tgtaatcaag ccatctggct    3540
ctactgtgaa ttctggcttg tctgccagtg ttccgtctgg tttgaggtag taccagcctg    3600
ttccgtccgc tgactggata aaggcatttg ataccatggc gccttcttta gcgtctaagt    3660
agtaccaagt gtccttgtac ttgacccagc ctgtcttcat ggcaccttct tcgttgaaat    3720
agtaccactt atcagcgatt ttcttccagc ctgtagccat ttcgcctgag ttgtcgaacc    3780
agtaccagtt gccgtctgtg tgcttcctcc agcggtctgc aagcatatag cctgaactgt    3840
caaagtagta ccaagtgcca ttgatttttct caaacttgtc ttttggataa gagccgtctg    3900
agtgtacgta ccagtagcca gtgtcattct cctgccagcc tgtttcaatc gtcaagccgt    3960
tctcaatatc atgcttaaac tgctcacggc taatgcccca ttttgccaag taagggtatg    4020
gatccacatg gtctgagtgg ttgtttggtt ggttattcgt gcaatactcg tgcgttttaa    4080
ttccagctaa actccctgta tcaagcgttt tcggcaaacc tgcttcatct gctagattgc    4140
```

-continued

```
gtaagagttc gatataaagg cggtagtccg tcatgaactc ttctttagtt gaatggcttt      4200
caatcagttc aaccgctgca taggtctcag cattccaacc gcccccaacg tcccaggcac      4260
cattatcaac aggtcctacc tgcatgatgc aaccgttccc aacaatgtgc gagaaaaaac      4320
taattctggg tctttccgcc agtgataatc cgcttcattc tgtacggttg aatgcggatt      4380
cccagttgag tgtgcgtgta cttgcctata tggttcacg ccgacttgag gcaaatctgt       4440
tcttaattta ctcacattaa tttccatatt ctactcctta tcaattaaaa caactcattt      4500
tttacaatcc aaaaccagaa actcctttat ttctacctta caaagaagac aatcttagtc      4560
acgattaggc ttgtagatag aacctcaaaa cgcactattt tgacactgta aataggactg      4620
acaaggtctg cattctatct acaataacac cccagactaa aaagcttttc aaagtatat       4680 ttttacagtc tctatatgtc cttttcataa atactatact ttattatatc atataaaga       4740 agtcaaaagt ctgttaaact attttcaaca ccaaactaaa gaagagaaca caagttttt       4800 cgatgttcac tagaggaaat ggattttatt cagtaaatcc aactaggatt gcactttggt      4860
tgccaaaatt gcctttcctt cttttatcaa gggatgacgg aatagtgaga agtcagttg       4920 aactgtcatg gcaacccaga taagaggttc acaaggata acacccttat atcctgccca       4980
aggaataatc aaaaccacaa aaacgatttt tccgattagt tcaataaagc tagaaactag      5040
aggaaggatc ttctgcccca agccctgcaa gcaatgcgat aaatcaacaa gagctcaaaa      5100
tggataaaag gctgaactgg atttgcagat agagacttcc attttctatc aagtaaccat      5160
ctgtcgaact agccaagaag gaaatcaagg ctgggctggc aaaaagagg aaaatacaaa       5220 caaaaactgc caggatata cttaaacgac tgccgattcg aagaccttga gcaatgcggt       5280
caggtcgctt agctcctaga ttctgagaag caaaggtcgt cattgatgca gaaatagcgg      5340
tcataggaag aagggcaaag gtcataatgc gtcgagctgc cgtctgggca ctaataatca      5400
ctgcaccaaa tgtattaaca gaagactgta aaatcacact gccgatagat acaattgaac      5460
tcatcaagcc catagccaaa ccttgctcca agagatccgc gtacaagctt ttgtcccatt      5520
tgaaatgttt aaactgtggc aagagttctg gcacactttt acgaatataa taaagcaga       5580 gaaccgctga taaaccttgt gaataatgg tagcaagtcc tgcggattga actcccagat       5640
gcaattgcgt aataaaatag agatccagaa ccacattaac caaggcagag aaaatcagaa      5700
atcccagggc tgctagactg tcaccaatag accgcaacaa gcctgcaaaa agattataag      5760
caaagctgac acctacacag gtcacaatca tagaaatata ttgataagat tgaagaagaa      5820
tttctgcag                                                             5829
```

<210> SEQ ID NO 5
<211> LENGTH: 3568
<212> TYPE: DNA
<213> ORGANISM: Artificial sequence
<220> FEATURE:
<223> OTHER INFORMATION: Synthetic probe

<400> SEQUENCE: 5

```
ctgcaggata tttctgcctt gtattgccag tggtttagcg ccacagccac atatctttta        60
cggtttttta ccgagaaaat caggtcagca gaagcaattt ttttggcttg aaaaaagatt       120
atcctgaaac acagattttt tatgaatcac ctcatcgtgt agcagacacg ttggaaaata       180
tgttagaagt ctacggtgac cgctccgttg tctctggtca gggaattgac caaaatctat       240
gaagaatacc aacgaggtac tatctctgag ttattagaaa gcattgctga aacgccactc       300
aagggcgaat gtcttctcat tgttgagggt gccagtcagg gtgtggagga aaaggacgag       360
```

```
gaagacttgt tcgtagaaat tcaaacccgc atccagcaag gtgtgaagaa aaaccaagct    420
atcaagggaa gtcgctaaga tttaccagtg aataaaagt cagctctacg ctgcctacca     480
cgactgggga gaaaaacaat aaagggagac aggatgtaat aattctgtct gtttctgttt    540
aacttaatta gtgatgataa tataaagatg tatcacttgg tatagaagct ttggtattaa    600
gttttttatt aagcccatac ggaataccga tggttggagc agcagttata gcgttcttag    660
aaggtataaa tagaaaaata aggtcatttt aaatcaaagg attgataaat cagaaagaag    720 gtgattttt gcgaacatac gaaaataaag aagaactaaa agctgagata gagaaaacat     780
ttgagaaata tattttagaa tttgataata ttccagaaaa tttaaaagat aagagagctg    840
atgaagttga cagaactcca gcagaaaacc ttgcttatca ggttggttgg accaacttgg    900
ttcttaaatg ggaagaagat gaaagaaagg ggcttcaagt aaaaacacca tcggataaat    960
ttaaatggaa tcaacttggt gaattatatc agtggttcac agatacctac gctcatttat   1020
ctctgcaaga gttgaaagca aaattaaatg aaaatattaa ttctatctct gcaatgattg    1080
attcgttgag tgaggaagaa ttatttgaac cgcatatgag aaagtgggct gatgaagcga    1140
ctaaaacagc gacttgggaa gtgtataagt ttattcatgt aaatacggtt gcacttttg     1200 gaactttcag aactaaaatc agaaaatgga agaagatagt attataaatt atattttaa    1260 ctttaaaaaa tttcataaaa atggttacca aaggcgatag aagaaaaact atcgtctttt   1320
tctttgcaaa tttttaagaa ggggaggtga tcttgcatgg actttgaata tttttataac   1380
agagaagcgg aaagatttaa cttcttaaaa gtaccggaga tattagttga tagagaagaa   1440
tttcggggct tatcagcaga agcaattatt cctttattcc atacttctta aacagacagg   1500
aatgtcattt aagaataact ggatagacaa ggaaggcaga gtatttatct attttactgt   1560
cgaagaaatt atgaaaagaa gaaatatctc aaagccaact gccataaaaa cattagatga   1620
gcttgatgta aaaaaggaa taggactgat cgaaagagta aggcttggac ttggtaagcc    1680
gaacatcatt tatgttaaga ctttatgagt atatttcagg taaaagaaaa tgacttacag   1740
aagtcaaaaa acttaacttc agaagtaaaa gattttaacc tcagaagtaa agaaaatgaa   1800
cttcaagagg ttaagaacct tgactctaac tatatagaga ataataagag taagtatagt   1860
aagagagaat atagttttgg tgaaaacgga cttggaacat ttcaaaatgt gtttttagct   1920
gctgaagata tatcggattt acaaatcata atgaactcac agcttgagaa ttacattaga   1980
ctttctgcaa aactagaatc ctagttcatg attgataata ccagcaatca aattcattcg   2040
taatccgaag cgtttacgat gattttgata ggttgttgaa acattttaa acgttttttac   2100 tttggcaaag atgttctcaa ccttgcttct ctccttagat agcgcatggt tacaggcttt   2160
atcttcaact gttagcggct tgagtttgct ggatttacgt gaagtttgtg cttgaggata   2220
tatcttcatg agcccttgat aaccactgtc agccaagatt ttaccagctt gtccgatatt   2280
tctgcgactc attttgaaca acttccatat catgacaata gttcacagtg atatccaaag   2340
aaacaattct cccttgactt gtgacaatcg cttgagtctt catagcgtga aatttctttt   2400
taccagaatc attcgctaat tcttttttta gggcgattga ttttacttc cgtcgcatca    2460 atcattaccg tgtcctcaga gctgagagga gttcttgaaa tcgtaacacc actttgaaca   2520
agagttactt caacccattg gctccgacgg agtaaagttg ctttcgtgaa taccaaaatc   2580
agccgcaatt tcttcataag ttcgatattc tcgcacatat tgaagagtag ccataagaag   2640
gtcttctagg cttaatttag gttttcgtcc acctttgcg tgtttaagtt gataagctgt    2700
ttttaataca gctaacatct cttcaaaagt cgtgcgctga acaccaacaa aacgcttaaa   2760
```

-continued

```
tcgtgcatca gttagttgtt tacttgcttc atcattcata gaactactat accatatttt   2820
gtttcgcagg aagtctattg gaaagtaaga aatattgaag ctgaggctat tagaagaaat   2880
tgtgagcgtg gtgctatttt ttcaggtaaa ataaaatatc acgaagattc acagtttaaa   2940
ggagatcact atgttgaatg ttatgctgtt ttagataata cggttatagc aagagataga   3000
ataacagtcc ctatcgatcc gttatgtgga aaagatttta tagagtagca tataattgat   3060
tcttaactgg aatactcact atctctttac atcaagaaaa tgactaaaca gggaagtttg   3120
ccttcttccc tttttttgtt atactagtag aagaaaaaat agaaagattt gtgggagtga   3180
aaagtcctgt ggactttttc agcctgagcc aagaaactcg aaagctcgta agtctgattg   3240 gcttttcaa tgtgaatctt aacttcatac tcccaaagag gtattagtgt cgtgtctcaa    3300
tcttatatca atgttatcgg tgctggtttg gcaggttctg aagcagccta cccaaaatcg   3360
cagagcgtgg gtattccagt taaactttat gaaatgcgtg gtgtcaagtc aacacctcag   3420
cacaaaacag acaattttgc tgagttggtt tgttccaatt ccttgcgtgg agatgatttg   3480
acaaatgctg ttggcctcct taaggaagaa atgcgtcgct tgggttctgt gattttggaa   3540
tctgctgagg ctacacgtgt tcctgcag                                      3568
```

<210> SEQ ID NO 6
<211> LENGTH: 4528
<212> TYPE: DNA
<213> ORGANISM: Artificial sequence
<220> FEATURE:
<223> OTHER INFORMATION: Synthetic probe

<400> SEQUENCE: 6

```
ctgcagattg gtatttatcg ccaccatctc cgtaagtctt agtacctgta aggacaattt     60
tcttagcctt aattgtctta ccaaaatcaa tgtcttttgg cttattgtta tctggccaat    120
cagttgcagt aaaggtatgc tccttgccag actcatctgt cacaacaagt ttcacatcac    180
gcaagttacc atttgaacct gatccacgtg aacataacg aagtccagtg atttcagttg     240 cttcttcaa gaccatggtt gcaggcttgc ctacatctcc tccgcccat gatgtatgcc      300 ataaactaga taagtttcca tcaaaggcat ttgcaagacc ttcttgagcc tgagcaggag    360
ctgtaagact tgcaaagtca tctgctacca agccgtttt cttctgaacc aaagcattct     420
tcaaggcttc aatcttggca atctctgcac gcgcttcttc cacactgata tcatcatcgg    480
cctgactgag gttaaagacc gcctctttca aagcatccat agactctttg gtgtagttag    540
tcatggcaac cgttggcaag tagttcttca gagcattttc tgtcaacatc ttacctgtta    600
gggtaatttc ttcgatttga agattatcca tcatgaagtc gttataacca cggaagttgg    660
catttccacc agaatcacca cgagtattac ttgcatttcc agttgagtag atacctaccc    720
aagtatcccc tgtttctgca cctgtcacga ggaaggttgc cttcttggct ttcttagaat    780
ctgtccaagt atttggcaat tcatgcattt ccaagttgct tgcttgagta ccacgacgac    840
ctgactggaa ttctccctta ccgactacaa agcataggg attgtctgaa cctgcttcgt     900
attcaaaggt tacacggtag gtcttacctg cttcaaaacg gaagttttgc ggaatagttt    960
ggtaaaccaa gttacgacgg ctcactagtc catttgtctt gagtgaccaa tttccttcga   1020
taacatcatc gactttctta ccattccaac cacgttgtgt atatggatcg tgttttcag    1080 acaagtgagt gcggttgtct tcgacaccct cgacaccacc cactacaaat gggaagatac    1140
cctgagcaac attttcaaag tcttgcttga aggtgccttt acctgtatca tgcttgtctc    1200
cgtacatgct tgaattgttt tcaaaggtac gaatttcatc aaagtaagtt gcttcatcac    1260
```

-continued

```
cagcttcacg actcaatgtc agagtaacat ttgatacgtc cgatccagtt gtaaagaagg    1320
cgtacatgtt ttggaagtaa cttgtatcgt caactgtagc attgttacga cgtgtattgt    1380
gggcataggc ttttacatag ttgagggcga gagacttatt ggtataagta gtcacttctt    1440
tttcaccagt atttacagtg atgctcgcct tggcattact acggttatcg acaccgacat    1500
aaacggcata cttggtattt ggtttcaagc cagttaattt ctgagtgaga ctaactttt     1560 ctttgtttcc ttgaatacga agcatatcgt ttgccccttg agacttgaca atttctgcct    1620
tagaagcatc gcctgaaatg gtccaatgtt tcaaggtacc actgttaaat ccttggtcat    1680
agatgtgcat gccttcactc catgacattt caggattggt ttgtttcgaa cgatagagaa    1740
cgtatggttg atttgctaga agatctaggg taatttttacc atcttttaca gttagttctt    1800
gctcttctgt cttaccttgg tcagttagct tgtaaaggta aaccttgctc tttgcccaat    1860
cgcttggaag ggtccaagtt gttgcaccgg cctgcgtatt gaagtagtac atcttttcct    1920
tatcagtaga aagtttctta ccatttgcat cccagttcca aggagtcaag taagctgaac    1980
catcttggat gacacgtccg ttgagagtta ctgtacgttc gcgatattgt ggactattga    2040
catcatttga cttacgagtt acaactactt tattattgtc agcatctacc aattccactc    2100
gcatttctgg agtccattta taggtgctac cgttatcggt catagtccac cggtgtacca    2160
ttttcccatt tacttacagt gaagtgttgg aagtacttgg tcatgacgtc atgggcaaat    2220
aagttagtta catagccatt gtagtcactt cttccttgcc agccttcaaa gtctttcatg    2280
ctgtagccac ctagcagtgg atagttggct gcaccaccat aacttctgta gtcccctacc    2340
caagcatctt tttggtggtt acgtataaag cgggtgatgg cactgttgat acctttattg    2400
gtgtagccac cgtaggtcaa gtcagctgcc cagtgatgga aggtagagtc gtactcacca    2460
ccatggcccc actcgatcgc aaagcgccag ccttgtttgt taatttcttt agcaagaacg    2520
tgggtagccc aggcaccgtt atcacctgat tgaccattac cccaaacgtc cacatagata    2580
aagtcgagac cgtcaccaag ttttttcttc aaatcttccc aacgtgccaa cgaccatga    2640 gctaggtcat aggcagcatc aatgttgata ccttgatcta gccagttcca accatagcta    2700
tagcttccat ctggattctt acggagaatt ttttcattga agtatttaga ctcaggataa    2760
gtttctgaag cgttaacgtg gatacctaga tgagctccat atttcttagc cttctcaatt    2820
agggtcttga agtcttcgac accaccgata cgcttaccaa tatcagcata gttcaagtga    2880
ccagagtcat ggccttcgct accatatcct ttaaggagaa caccttgccc aagaccatct    2940
gtgtggagat tgattttctt gataccatcc aaggtcataa ggaatgggtt ttgtgcttga    3000
gaaccaaagt tcatcgcgat acggtaagct gtgatatcct taactttttt ccaaccttga    3060
ggattgttca taatgctacg ataagcaatg gcaccatcct gccaatcgac tttcttgtct    3120
gcattggcat cttcagtgat aacaacctta gcacttggaa gttccttcgt gtattctggg    3180
aaaacaatgc ccttataagc ttttttccat tgccattcag agctgtggat tcctacatag    3240
ttggcatttc cgactgtttc tttataggct gtcaaacgag tccagtcatt cgaaccacca    3300
ccatagctgt tttgagagtt actccaaaca ccagcagcaa gcttatctgt agaaacaaat    3360
ccatacatgt aacccttggc tagatctttc attggattgg ttacatcgat atgatcatct    3420
ccgctgacat gcgtattgtt tgacatggtt gccccatcaa acttagcacc agtttgatca    3480
ctagaaacag agactaaagc attgccgagg aaactaatag aagaaagtag ttttcttcg     3540 tcatcaatct tttgacctgg agtgacttga ttgtggttga caatcttggt cacatcaaag    3600
tgcaattgat tgtccacaac ttgcaagcgt actgtcattt ccgcattgat taagtgagca    3660
```

-continued

```
tcatcgcgaa gcttcatcaa gtactctgct gttgtctcat tgattttctt ataagtgact      3720 tcagggtga ttcggtggtt attgataaag acttggttga actgttgaac ctgtcctggc      3780
aaagtatgtc cattcaagct gtattccttg acacgaggga aggcttggtc aatcactgct      3840
ttgagaacct tagactgaat cgtgtcataa gtcaccttgc tatcatcaac ttcaggacct      3900
gtttcttttt cagcaggggt atcctctgtt tttacccct cttggttatc cgttttaacg       3960
ctaacaactg ttcgctcatc gtcataagag cccgccttga aagaatctt cttctcattt       4020 ttaagatggt cattgaccgc agctggtaga gtcactgtgt caaagagatt gacatcgtta      4080
ttgctggcat ttagctgacc gtctgacttg agagtgatag agagacggtt tgtgatctgt      4140
ttcagagcag caacacgact acctctatac caagtgctag ttgttggaga tttatactcc      4200
cagaaccagc catccttgtc ataaccgaca aaacattat tcttggtatc tttaaatttc       4260
aagaagacac caaagcgtga tttgcccttt tcagaatcat ctttgaaggt taaatcaaca      4320
gttgcatttc cattggcatc aacggtcaag cccttctttt caaacagggc tggtttacct      4380
gcgttatcat tttgagcagt tgaggataat tggttgtagc ggacacctt ttcttctcgg       4440 atagtgactg ttccctgttg ttcttttttc tctaccgttt gccattcagg ggttaccgtc      4500
ttaggtgttt caggtttagc agctgcag                                         4528
```

<210> SEQ ID NO 7
<211> LENGTH: 5579
<212> TYPE: DNA
<213> ORGANISM: Artificial sequence
<220> FEATURE:
<223> OTHER INFORMATION: Synthetic probe

<400> SEQUENCE: 7

```
ctgcaggctt cccttttagca gttacagcct gtttcttacg gtcttttttca ctccggccaa     60 tcggcgcttc aattcacca cgatcattag gcagatttcc atgaacaatc gcccaatatt       120
tgcggagaga cttttttatct ttgagttctt ggcaagtac tagatgcgca tcatcgtttt      180
tagcaatcat gagaagacct gacgtatcct tatcaatacg gtgaacaatc cctggacgca     240 gaacccccatt gatacccgac aagtccttaa tatgatacat gagggcattt actagggttc    300
cactggtatg accagcactc gggtgcacaa ccattcctg aggttttgtta acgacagcca    360 catcctcatc ttggtagact atttctagcg gaagatcctc agccacatac tctaatacct   420
ctggttctgg cacatggtaa gtgacgacat cacctcttg gactgtgtat ttagcttttct    480 tgacttgacc attgaccaag acctggcctg atttaatttg ttcattcgcg agactacgtg    540
ataattctga caaatctgac aaagccttat ccaaacgcag accaccagtt tcaattttaa     600 tttccatta tttcctcttt tagcattgca atcaataaaa taatcactcc aaccgtcaga     660
tagctatctg ccacattgaa aattgcaaag ttgataaagt caaggtggaa catatccaca    720
acaaagccct gactgaccct gtcaataaag tttccaagac caccgcgat tattagagtc     780 aaacccaaga ccatccagaa tgagtcctcc atgtgtttat gtaaatacca aatggcacct    840
atcacgacaa ccagagtaat gacagcgaat aacagctgct gatcttgtaa gatagaaaag    900
gctgcacctc gattttgcag gtaggtcaag ctaacgaaat tgggaatcca ggagcgcact    960
tcacccagtg gaatctgctg gacgatatag gatttgacca actgatccag cccaattaaa    1020
agcagtacaa tgactgccac tattgctctt ttttcatga tttcctcttt tgatcaaaat    1080
attcttgcat gacttctacg aagagagtcc cagcttgact aagctccact tcttcacgtt    1140
taacatagac catgcggtta tctaggttat ccttgagacg aataactgta atgccattaa    1200
```

-continued

```
cactgtcact atctaaaaat ccagaacctg tcgcataggc gtccgtccgc tccaaaatac    1260
cattcaaggt ggcacggtct gtcacattaa acatctgtga gctagcgctg gtatcgacaa    1320
agttctctga ataataaagg tactcgtctt tctcttgagt gaaacagacc gttggtaaat    1380
ccgctaaatc ctccatgact aattcctctt tctgggctaa aggatgaccc tcacagagat    1440
aaatatgggt atggaaggaa tcaattcgat gacctccaga cctaactttt caacccgttg    1500
cataatcccc ttttattttt gattgtggag gtagataatc ccaatctcac tatgcccttg    1560
cgccacttca tctaatattt gaacagtagt tgattcaaaa atacggaagt tcttatagtc    1620
aggatagcgc tctgaaaagg ccgtaatagt tggtggtaag aagtcatagt gctggctagc    1680
aacggaaaat tcatcttttt cttcttcagg attggcatac tgattttgaa aaatatcaaa    1740
tcctttaacc aattcttgcg cttttttcata aaattccatc ccacgacggg tcaagaaagt    1800
ccctgagctg gtccgacgga aaatcttaaa gcccaactct ttttccaaat cacgaacaga    1860
aatagacaga ctcggctgac taacatacat cttttcagca gcttcacgaa aagtaccact    1920
attggcaata gccacaacat agcgtaattg ttgaatgttc atcttctacc cccaacttct    1980
ttatcttttc attataccat attttagaag ttttccaaaa aggaaaaaag aacatcctat    2040
tcttcttaac tatcttcact atctgccttt ctcacgccaa tcttattttc aaaatcaatt    2100
caaaaaaata agtggctaca caccacttca gtatcggaaa gaaaaacgtt gactatttgt    2160 gaaaaagaa atgccggaa aattccgaca ttttttagt aagctaactt cctgaaaata    2220
ggagtaacca aacatcccag aaggcagtga tattgatgag aatatgaact agtattggat    2280
agtagagatt tttagtcatg cgatacaata gagctaaaat cagacctcca ctagcataaa    2340
tgaaaaaagc aagaggagtt aaagcaaaat tgatatgaat ataaccgaaa ataatagcag    2400
aaagcaaaac atctccgtac caaggtgagt ttttgaaaaa ggttgtcata agcacacctc    2460
gataaatcaa ttcctcagca ataggggcga tgaagcaaac gatgagcaag aaataaggga    2520
actcctgtct ccccatcatt tctatcgttt cattcaaaga atctgatttt gaagacaggg    2580 atatgaaaata cgaaaagagg aagtcagaca tatatgaaat gatgtagccc agtaaaaggt    2640
agatgaagta cctcagctgc cacttgaaat gaaaaatttt cttcctgca aaaaccagta    2700 gatagatgac cgctaagaaa agaactccgc tctccatcaa aagcagaatc tgaaaaaatt    2760
cacgacttgc tggtagatag ggctttgcga ggtgattgaa aactctccaa aaccaagttg    2820
atttgtaaaa aattaaggac aatgctagta aaatttgaat agcccgtttt ttcatattaa    2880
attctctgct ttctccccct gtttcttcat attactaata aattttactt aaaatctcgc    2940
agcacttcct ttgcaaagat gattgcctcc tccaatatat cctaaatcat aggtgcctct    3000
gggacaaaat ccatgaaccg gcagagttaa tactggttct atttcccaat cgtacctacc    3060
attaggattt ttaccatatg aatctgctcc accttgtatc agctctaatt cttcatttgt    3120
tagatttata ttttttgtca ttaaaatcat gatatatttc ctccattatt cttcagatta    3180
gttgagtaat ctgatactca tacctactta caaaaaaact attatattaa gttggttttt    3240
taatttgtct agttgcaaca ttgacaaaca tagtatagca tatctttgcg aaatatcctc    3300
ttcaaatcat gaattgtcat caaaacatct taaactataa aatcaattag tctcaagctt    3360
tctatcaatt tcttctccaa aatatgctat aataatagca aaagataaag aaggaagacc    3420
tatgattaaa ctactagcct tggatatgga cggcaccctc ctcaatgaag ccaaggaaat    3480
cccacaagct cacattactg ctattcacaa agccattgaa aaaggtgtca aactggttct    3540
ctgtacggtc gcccccttttt cggtgttcct ccctactac aaaaaactgg gactcgacct    3600
```

-continued

| | |
|---|---|
| ccagaatgag tatgtgattg ttaacaacgg ttgttcaact caccagacta gcgactgggg | 3660 |
| cttggttgac tggcaagaac ttagtccagc tgacatcgaa tacctctatg accttgctga | 3720 |
| aaagagtgat gttcagttga cacttttttga cgagtcacat tattttgttc tcggtggaaa | 3780 |
| gcccaatcaa gttattgaaa atgatgctaa actagtattt tcagacctga ctgaaatttc | 3840 |
| tcttgaggaa gcgactagtg gaaagttccg gatgttccaa ggtatgtttt taggaacaaa | 3900 |
| agaacaaaca gacgattttg agcagcgttt tgctgaagag ctttgccaac gattcagtga | 3960 |
| gttcgttcgc agcctgtcat ttatgaagca atgccacttg aacgacaaa ggctactgct | 4020 |
| cttcacgact agctgagatt ttgaagattg attcctcaga gattatggcc atgggcgatg | 4080 |
| ctaataacga tatcgaaatg ctccagtttg cagggcttgg gattgcaatg ggaaatgcca | 4140 |
| gcgattatgt caaatctctt gcggatgccg ttacctcaag caacgaagaa gacggcgttg | 4200 |
| cgcgtgctat tgagaaatat attctataaa aagaaaagc aaatagacag aagttactgc | 4260 |
| tatttgcttt tttgctaata ttttaaaata cggactaatc aatagagaag aatagcgaat | 4320 |
| cataaaaatc gatttactag atgccatagt atcttatagt tgctaataag aagttagtct | 4380 |
| agcagaatga atctctcatt tctcccacac taatctgtaa tttgtctata cattttctgg | 4440 |
| tcttctatct cgaaacaagc cccagtttag gcgttcactt gctcccttgt ctaggttata | 4500 |
| agtagctaac agaacagctt cttcttgtct ttcagctcgt tctagaatag ctcctgtttc | 4560 |
| atccgtcata aggaggaac cgtagaagtc aagactggaa ctctgtccgc cattttcctc | 4620 |
| actaggagta acctcctcta aaccataacg attggctgcg atgactggaa caatattcgc | 4680 |
| tgctgcgtgc ccttgcatag tacgttgcca gtgaccacaa ctatctgtat ccaaaattgg | 4740 |
| ctctgaaccg atagctgtag gataaaagag caattcagca ccattcaatg caagacagcg | 4800 |
| cgctgtttca gggaaccatt gatcccaaca gataccgata ccaatcttag catagcgagt | 4860 |
| attccagacc ttgaaaccag tgttaccagg cgtgaaatag aatttttctt gataataatg | 4920 |
| gtcatctggt atatgggtct ttcgataaac gcccagcact tccccatctg catcaatgac | 4980 |
| ggcaatagag ttatacaaga cattaccatc tttttcatag aaactgattg gtaaaacaac | 5040 |
| ttgtagttcc ttagcaatca ccttaaaatg ctgaatggca gtattttccg ctacagattg | 5100 |
| ggcatactgg tagtagtcat actgacgttc ctgacagaaa tagggatgtt caaacaactc | 5160 |
| gggcaagaga ataatttggg ctccttgctc agcagcctga cgtactaaac gctctgcggt | 5220 |
| ttggatattt gttgccacat ccttagcgca ttgcatctga atggttgcaa ctcttacatt | 5280 |
| tctcatcttt ttctcctatt ctggaatttg ttgggtgata cagtggatat tgccaccacc | 5340 |
| taagagaata tctctggctg gtattccgac aactttacgg tctgggaaac acttgctgag | 5400 |
| gatatctaag gccacttggt cgtttacatc ctcaaactgt ggaaccaaga cagccttgtt | 5460 |
| ggcgatataa aagtttacgt aggaagctgc tagtcgttca cctgcgtatc gctcttcttc | 5520 |
| tccttcttca tagatgtagc ctggcaaatc ttcttctgtc acaacttgtc gaactgcag | 5579 |

<210> SEQ ID NO 8
<211> LENGTH: 24
<212> TYPE: DNA
<213> ORGANISM: Artificial sequence
<220> FEATURE:
<223> OTHER INFORMATION: Synthetic primer

<400> SEQUENCE: 8
cgacgttgta aaacgacggc cagt                                          24

```
<210> SEQ ID NO 9
<211> LENGTH: 17
<212> TYPE: DNA
<213> ORGANISM: Artificial sequence
<220> FEATURE:
<223> OTHER INFORMATION: Synthetic primer

<400> SEQUENCE: 9
caggaaacag ctatgac                                                    17
```

PROBE FOR DIAGNOSING INFECTIOUS DISEASES

This application is the national stage of International Application No. PCT/JP95/02036, filed Oct. 2, 1995.

FIELD OF THE ART

The present invention relates to a probe which is useful for detecting and identifying the causative bacteria of infectious diseases, especially *Streptococcus pneumoniae* which is a representative causative bacterium of bacterial pneumonia.

BACK GROUND ART

In pathology, infection is defined as an invasion and an establishment of an anchorage for growth in a host organism by a pathogenic organism (hereinafter referred to as "bacterium"). The outbreak of a disease caused by proliferation of a bacterium in vivo depends upon the interrelationship between the resistance of the host organism and the virulence of the bacterium.

To improve therapeutic systems for treatment of infectious diseases, especially inflammatory diseases caused by *Streptococcus pneumoniae* and the like in pulmonary lobes and bronchia, namely bacterial pneumonia, among the infectious diseases, has been urgent problem in the field of this art. Such bacterial pneumonia is triggered by an attack with bacteria, e.g., *Streptococcus pneumoniae, Staphylococcus aureus* and the like which cause inflammation predominantly in alveoli. When suffered from bacterial pneumonia, generally from clinical aspect, inflammatory symptoms in upper airway followed by sudden chill and shiver attach, then crisis of high fever around 40° C., and terrible cough, stethalgia and sputum have appeared.

Further, the bacterial pneumonia is a serious and exigent infectious diseases in which severe systemic symptoms such as malaise, anorexia and headache have involved, presenting dyspnea, cyanosis, and could be accompanied by bacteremia, cerebrospinal meningitis or arthritis as the complication thereof, finally could sometimes lead to a lethal process.

Thus, improvement in rapid method for therapy of bacterial pneumonia has been awaited since appropriate therapy to be put into practice in early stage based on accurate and quick diagnosis is necessary.

Moreover, when suffered from an infectious disease including pneumonia, it has been believed that phagocytes including neutrophils, monocytes and macrophages primarily function in defense of the body, and that exuded bacteria from the texture of the phagocyte which had predominantly grown have appeared into blood.

In general, bacterial pneumonia is defined as a case wherein the ability of phagocytosis by cells cannot overcome the virulence of the bacteria and then the bacteria such as *Streptococcus pneumoniae* settle on the pulmonary lobe and the tissue of bronchia to cause inflammation. In conventional method for diagnosing bacterial pneumonia, the following items should be checked: 1) clinical symptoms; 2) culture of a specimen; 3) gram-staining of the bacteria contained in the specimen; and 4) shock state. After those items have been clarified, the course of therapy has been oriented. In its typical case, the above mentioned clinical symptoms, stethendoscopic findings, and increase in neutorophils, increase in acute phase response substances such as CRP (C-Reactive Protein) make speculation of diagnosis possible, however, for definitive diagnosis, the causative bacteria must be searched and determined from the specimen such as sputum, hydrothorax or blood, and then treatment must be conducted using proper antibiotics responding to the species of the bacteria. Accordingly, rapid and reliable identification of the causative bacteria has been awaited in the clinical site.

Additionally, novel types of pneumonia e.g., Legionellosis and *Pneumocystis carinii* pneumonia are identified, and resistant strains such as MRSA (methicillin-resistant *Staphylococcus aureus*) have been appeared recently, the importance in searching the causative bacteria have been growing.

However, as a matter of fact, difficulties have usually accompanied in confirming the causative bacteria. Especially, in case of community acquired pneumonia, it is known that therapy is initiated in 30–50% of the cases under such circumstances wherein the causative bacteria thereof are not clarified yet. As a method for identifying the causative bacteria in a patient who is suspected to be suffered from bacterial pneumonia, the following common procedures are adopted: employing the sample collected from sputum, secretion from upper airway, hydrothorax, topical focus, or blood as a specimen to estimate applicability of the sample as a test material by observing inflammatory cells of smear thereof, then, determining cell type by Gram staining e.g., gram negative or positive, and coccus or bacillus, and finally, culturing the bacteria using selection medium to identify the causative bacteria.

In accordance with this method, however, culturing the bacteria takes long time, and contamination of indigenous bacteria could not be avoided as well. Otherwise, in case that a lot of antibiotics have been administered when bacterial pneumonia had been suspected, even though bacteria are contained in the specimen, proliferation or growth would often be prevented, thus the rate of success in culturing the bacteria from the specimen has become actually quite low.

Although available subroutine methods including instrumental analysis method of constituents of bacteria and metabolic products by bacteria (See Yoshimi Benno, "Quick identification of bacteria with gas chromatography", Rinsho Kensa, Vol. 29, No.12, 1618–1623, November 1985, Igaku Shoin.), a method utilizing a specific antibody (See, Japanese Patent Provisional Publication No.60-224068.), and a hybridization method utilizing a specificity of DNA (Japanese Phase Patent Provisional Publication No. 61-502376) have been developed, any of which requires separation, culturing and growing of the bacteria.

On the other hand, as an established method based on the function of the phagocyte in infectious diseases, there is a method to examine a stained smear of buffy coat wherein leukocytes in the blood sample are concentrated, under an optical microscope. Generally speaking, the rate of detection of bacteria in buffy coat specimens from adult bacteremia patients is 30% at most, which is similar to that in blood specimens from an earlobe. However, it was reported that in case that the patients were newborn children, bacteria had been detected in seven cases in ten cases total (70%). Therefore, information concerning the presence of bacteria in peripheral blood obtained by a microscopic examination on a smear is an important index for therapy.

Since the above mentioned conventional methods necessitate the pretreatment which requires at least three to four days in total including one to two days for selective isolation of bacteria from a specimen, one day for culture, and one or more days for operation of fixation, and then the culture thereof is continued in practice until the bacteria grow. Therefore, in many cases, the pretreatment requires one week or more. Furthermore, there has been a risk on contamination of a other bacteria which could not be distinguished from the causative bacteria during the culture period.

As an important matter, under such circumstances above described, the number of bacteria that can be grown is small even under appropriate conditions for culture, because many bacteria in a specimen to be grown have been ingested into phagocyte, dead or on a static state due to antibiotics administered. Therefore, the actual detection rate of bacteria is as low as about 10% when the clinical specimen culture method is employed. In the other words, for the present, the presence of bacteria in 90% of the examined blood from the patient suspected clinically as suffering from pneumonia, which has been cultured for further one or more days, could not be proved after all.

Thus, in light of the situation above, the present practice depends on a trial and error treatment method, starting when pneumonia is clinically suspected without awaiting the detection results of the identification, wherein an antibiotic having the effectiveness for the widest range of the causative bacteria is administered first while the causative bacteria is still unknown, and if the antibiotic is not effective after one or two days, then another antibiotic will be tested, regardless of the fact that determination of the causative bacteria and selection of the suitable antibiotics are required.

According to the method to stain the bacteria in a specimen, the constituents of the living body are likewise stained together with bacteria, therefore, a skilled experience to identify bacteria quickly according to their image through a microscope is required, then there may be cases that can be hardly identified.

Although pneumonia is a disease wherein a rapid and exact diagnosis has been required as stated above, the conventional diagnosis method could not have satisfied such requirements.

SUMMARY OF THE INVENTION

The present invention was accomplished in view of the above-described problem in the art, and according to one aspect of this invention, there is provided a probe having a specific reactivity with DNA or RNA obtained from causative bacteria of the infectious diseases, especially, *Streptococcus pneumoniae* which is the representative causative bacteria of bacterial pneumonia, and nucleotide sequences of a portion of the gene essentially included in *Streptococcus pneumoniae* being elucidated.

Namely, the probe of the present invention allows significant detection of remaining bacterial DNA, the bacteria being incorporated into phagocytes and destroyed, thereby quick and accurate detection method of the causative bacteria of the infectious diseases would be available without culture and/or growth of the bacteria. Moreover, when a primer is designed with reference to information on the nucleotide sequence of the probe, causative bacteria can be identified without hybridization step, through amplifying DNA by means of a PCR technique.

Additionally, when a non-radioactive probe, e.g., a biotinylated probe, is used for hybridization step, detection in a general laboratory can be performed as well using an optical microscope, and the detection process will be carried out rapidly and simply.

BEST MODE FOR CARRYING OUT THE INVENTION

Examples of the probes from *Streptococcus pneumoniae* which is a causative bacterium of infectious diseases, especially of pneumonia are described below:

EXAMPLE 1

DNA Probe from *Streptococcus pneumoniae*
(1) Preparation of DNA Probe from *Streptococcus pneumoniae*

Clinical isolate of *Streptococcus pneumoniae* was cultured overnight in BHI (Brain Heart Infusion) medium, then bacteria from the culture were collected, added thereto N-Acetylmuramidase SG. Thereafter genomic DNA was extracted according to Saito-Miura's Method ("Preparation of Transforming Deoxyribonucleic Acid by Phenol Treatment", *Biochim. Biophys. Acta,* Vol.72, pp.619–629 (1963)).

The extracted DNA was digested completely with restriction enzyme PstI and random cloned into vector pGEM-3Z. Among thus obtained clones, seven probes unique to the bacteria *Streptococcus pneumoniae,* namely probes comprising DNA fragment showing specificity to DNA from *Streptococcus pneumoniae* were then selected.

Figure 1:
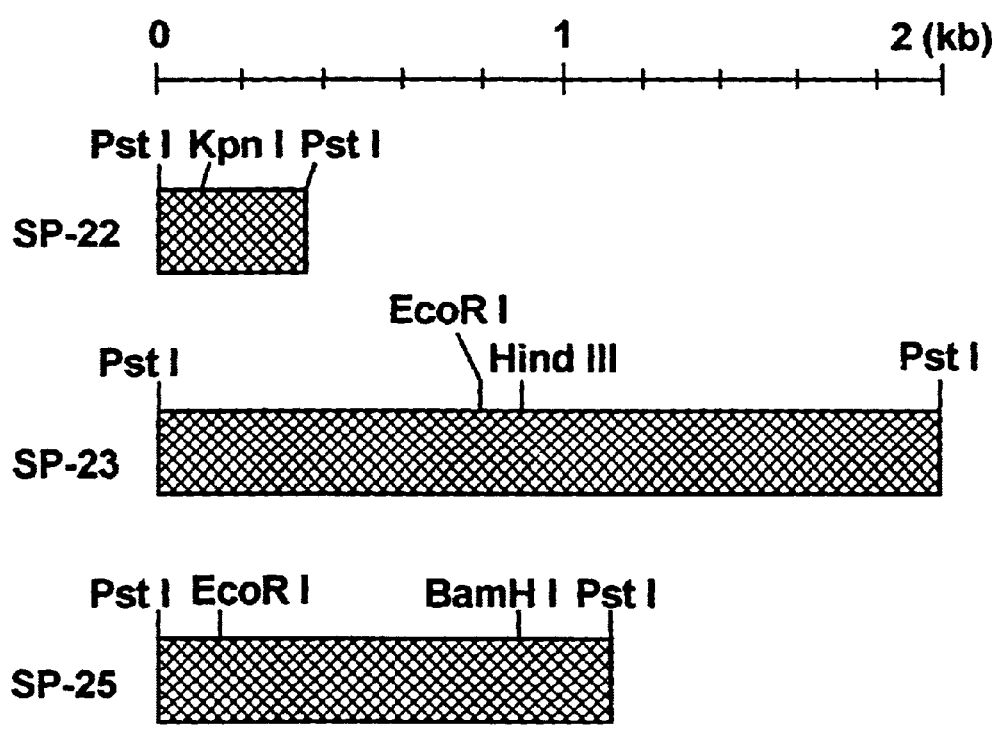
FIG. 1 illustrates restriction enzyme maps of probes SP-22 (SEQ ID NO: 1), SP-23 (SEQ ID NO: 2), and SP-25 (SEQ ID NO: 3) for detecting *Streptococcus pneumoniae.
Figure 2:
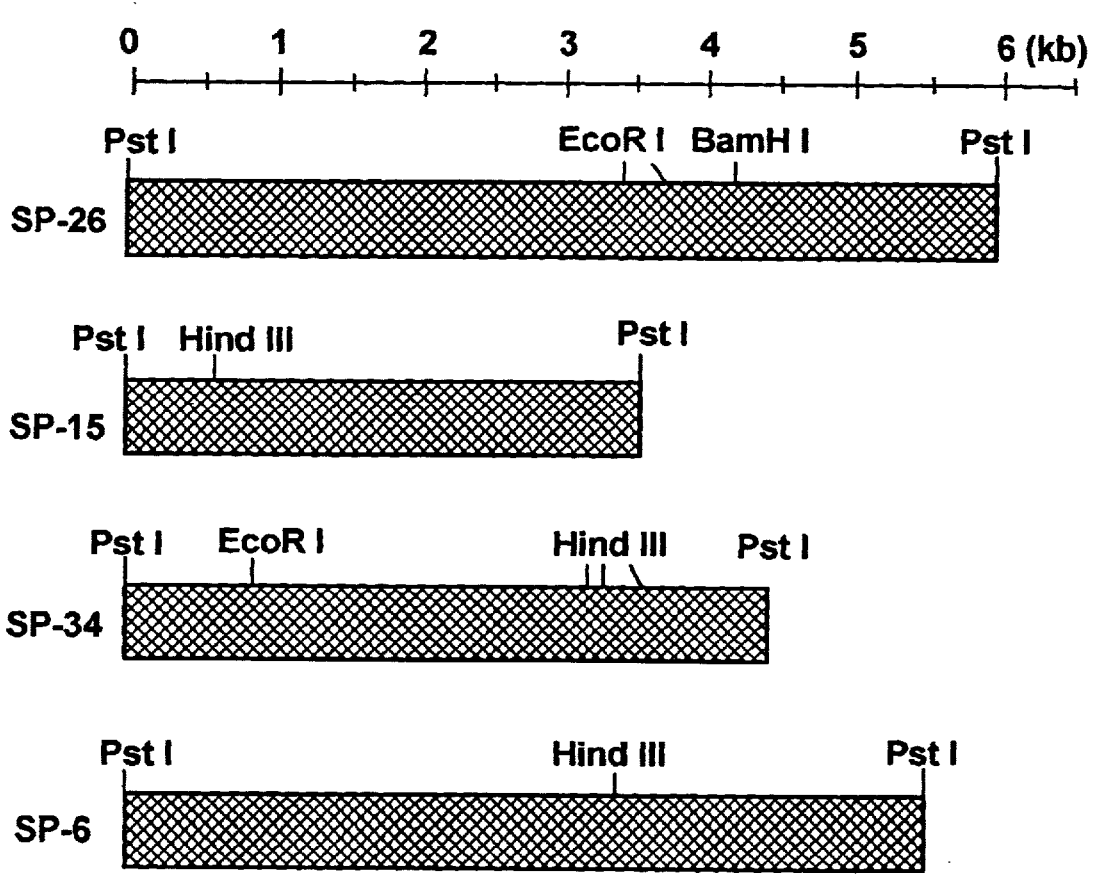
* and FIG. 2 illustrates restriction enzyme maps of probes SP-26 (SEQ ID NO: 4), SP5-15 (SEQ ID NO: 5), SP5-34 (SEQ ID NO: 6), and SP6-6 (SEQ ID NO: 7) for detecting *Streptococcus pneumoniae.*

The selected probes were then designated as probe SP-22, probe SP-23, probe SP-25, probe SP-26, probe SP-5-15, probe SP 5-34 and probe SP-6-6 (SEQ ID NOS: 1–7, respectively), and restrictions maps of which are illustrated in FIG. 1 and FIG. 2.

Reactivities between each probe and DNA from several kinds of causative bacteria of infectious diseases were examined according to the following method.

First, as subject strains for an examination, strains of clinical isolate and deposited strains described below in Table 1 were prepared. Human genomic DNA and control sample in Table 1 were obtained and prepared from leukocyte collected from four healthy adult men, and *Escherichia coli* K-12 JM109 transformant comprising plasmid pGem-32, respectively.

TABLE 1

| bacterium No. | strain name | original source |
| --- | --- | --- |
| 1 | Streptococcus pneumoniae | NYSDH DP-2 |
| 2 | Streptococcus pneumoniae | clinical isolate |
| 3 | Streptococcus pneumoniae | clinical isolate |
| 4 | Streptococcus agalactiae | IFM 58/59 |
| 5 | Streptococcus anginosus | NCTC 8787 |
| 6 | Streptococcus constellatus | ATCC 27823 |
| 7 | Streptococcus equisimilis | NCTC 8543 |
| 8 | Streptococcus faecium | NCTC 7171 |
| 9 | Streptococcus faecalis | ATCC 19433 |
| 10 | Streptococcus mitis | ATCC 9811 |
| 11 | Streptococcus morbillorum | ATCC 27824 |
| 12 | Streptococcus pyogenes | DHI S8 |
| 13 | Streptococcus sanguis | ATCC 10556 |
| 14 | Streptococcus salivarius | ATCC 7073 |
| 15 | Staphylococcus aureus | ATCC 25923 |
| 16 | Staphylococcus epidermidis | ATCC 12228 |
| 17 | Escherichia coli | ATCC 25922 |
| 18 | Klebsiella pneumoniae | clinical isolate |
| 19 | Pseudomonas aeruginosa | ATCC 27583 |
| 20 | Enterococcus agglomerans | clinical isolate |
| 21 | Haemophilis influenzae | clinical isolate |
| 22 | Candida albicans | IFM 40083-A type |

TABLE 1-continued

| bacterium No. | strain name | original source |
|---|---|---|
| 23 | Aspergillus fumigatus | MTU 06001 |
| 24 | Cryptococcus neoformans | MTU 13001 |
| 25 | Mucor spinosus | TIMM 1322 |
| 26 | human genomic DNA | |
| 27 | control | |

[note] NYSDH ; New York State Department of Health (Albany, New York, U.S.A.)
NCTC ; National Collection of Type Cultures (London, England)
DHI ; Dairen Hygienic Institute
IFM ; Chiba University, Eucaryotic Microorganism Research Center
MTU ; Tokyo University, Medical Faculty
TIMM ; Teikyo University, Medical Fungus Research Center Then, DNA of each strain was extracted according to the method of the above Example 1 (1), and samples for dot-blot-hybridization were obtained by spotting certain amount (e.g., 5 μl) of the extracted DNA to a nylon filter and then conducting alkaline denaturation.

Human genomic DNA sample was prepared from the above-described leukocyte employing Saito-Miura's method (supra). Meanwhile, control sample was prepared from the above-described *Escherichia coli* K-12 JM109 transformant comprising plasmid pGem-32 applying the method for preparing plasmid DNA described in Example 2 (1) below. Hybridization on DNA probes from *Streptococcus pneumoniae* labeled with Digoxigenin-11-dUTP (BRL) was then performed overnight according to Manual of Maniatis (T. Maniatis, et al., "Molecular Cloning (A Laboratory Manual)", Cold Spring Harbour Laboratory (1982)), under the condition of 45% formamide, 5×SSC, 42° C.

Samples obtained by overnight hybridization were washed twice with 0.1×SSC, 0.1% SDS for 20 minutes at 55° C., then, hybridization was evaluated by detection through color reaction using Anti-Dig-ALP conjugates (BRL). Experimental results on hybridization between each of the probes and DNAs from each clinical isolate are summarized in Table 2 below.

TABLE 2

| | | | probe [denotation: SP-] | | | | | | |
|---|---|---|---|---|---|---|---|---|---|
| No. | bacterium strain name | (origin) | 22 | 23 | 25 | 26 | 5–15 | 5–34 | 6—6 |
| 1 | Streptococcus pneumoniae | (NYSDH DP-2) | + | + | + | + | + | + | + |
| 2 | Streptococcus pneumoniae | (clinical isolate) | + | + | + | + | + | + | + |
| 3 | Streptococcus pneumoniae | (clinical isolate) | + | + | + | + | + | + | + |
| 4 | Streptococcus agalactiae | (IFM 58/59) | − | − | − | − | − | − | − |
| 5 | Streptococcus arginosus | (NCTC 8787) | − | − | − | − | − | − | − |
| 6 | Streptococcus constellatus | (ATCC 27823) | − | − | − | − | − | − | − |
| 7 | Streptococcus equisimilis | (NCTC 8543) | − | − | − | − | − | − | − |
| 8 | Streptococcus faecium | (NCTC 7171) | − | − | − | − | − | − | − |
| 9 | Streptococcus faecalis | (ATCC 19433) | − | − | − | − | − | − | − |
| 10 | Streptococcus mitis | (ATCC 9811) | − | − | − | − | − | − | − |
| 11 | Streptococcus morbillorum | (ATCC 27824) | − | − | − | − | − | − | − |
| 12 | Streptococcus pyogenes | (DHI S8) | − | − | − | − | − | − | − |
| 13 | Streptococcus sanguis | (ATCC 10556) | − | − | − | − | − | − | − |
| 14 | Streptococcus salivarius | (ATCC 7073) | − | − | − | − | − | − | − |
| 15 | Staphylococcus aureus | (ATCC 25923) | − | − | − | − | − | − | − |
| 16 | Staphylococcus epidermidis | (ATCC 12228) | − | − | − | − | − | − | − |
| 17 | Escherichia coli | (ATCC 25922) | − | − | − | − | − | − | − |
| 18 | Klebsiella pneumoniae | (clinical isolate) | − | − | − | − | − | − | − |
| 19 | Pseudomonas aeruginosa | (ATCC 27583) | − | − | − | − | − | − | − |
| 20 | Enterococcus agglomerans | (clinical isolate) | − | − | − | − | − | − | − |
| 21 | Haemophilis influenzae | (clinical isolate) | − | − | − | − | − | − | − |
| 22 | Candida albicans | (IFM 40083-A type) | − | − | − | − | − | − | − |
| 23 | Aspergillus fumigatus | (MTU 06001) | − | − | − | − | − | − | − |
| 24 | Cryptococcus neoformans | (MTU 13001) | − | − | − | − | − | − | − |
| 25 | Mucor spinosus | (TIMM 1322) | − | − | − | − | − | − | − |
| 26 | human genomic DNA | | − | − | − | − | − | − | − |
| 27 | control | | + | + | + | + | + | + | + |

[note]
"+" denotes that the hybridization signal was detected,
"+" denotes that the hybridization signal was not detected, respectively.

Apparently from Table 2 above, any of the probes exhibited reactivity specifically with only DNA obtained from *Streptococcus pneumoniae*, and did not exhibit cross-reactivity (ability to hybridize) with any DNA obtained from bacteria other than genus Streptococcus, as well as DNA from other species of Streptococcus, thus specificity thereof to the species *Streptococcus pneumoniae* has been confirmed.

EXAMPLE 2

Analysis of Nucleotide Sequence

Nucleotide sequences of DNA probes (7 probes total) of which specificity to the bacterial species were verified in the Example 1, were determined according to the following method.

(1) Preparation of Plasmid DNA

*Escherichia coli* K-12, JM109 transformant, comprising the subcloned insert fragment (to be sequenced) in pGem-3Z (Promega), was inoculated in 5 ml of Luria-Bactani Medium (bacto-tryptone, 10 g/1 L; bacto-yeast extract, 5 g/1 L; NaCl, 10 g/1 L; adjusted pH to 7.0 with 5N NaOH) and cultured overnight.

Culture medium was centrifuged (5,000 rpm, 5 min.) to collect the bacterial cell body. One hundred $\mu$l of a solution of 50 mM glucose/50 mM Tris-HCl (pH8.0)/10 mM EDTA containing 2.5 mg/ml of lysozyme (Sigma) was added to the precipitate, and left at room temperature for 5 minutes. To the suspension thus obtained, 0.2M NaOH solution containing 1% of sodium dodecyl sulfate (Sigma) was added and mixed therewith. One hundred and fifty $\mu$l of 5M potassium acetate aqueous solution (pH. 4.8) was further added thereto and mixed, then cooled on ice for 15 minutes.

The supernatant obtained by centrifugation (15,000 rpm, 15 min.) of the mixture was treated with phenol/CHCl$_3$ and added thereto ethanol of two times by volume, then the precipitate was obtained by further centrifugation (12,000 rpm, 5 min.). This precipitate was dissolved in 100 $\mu$l of solution of 10 mM Tris-HCl (pH7.5)/0.1 mM EDTA, and added thereto 10 mg/ml RNaseA (Sigma) solution, then left it at room temperature for 15 minutes.

Three hundred $\mu$l of 0.1M sodium acetate aqueous solution (pH 4.8) was added to this preparation and treated with phenol/CHCl$_3$, then the precipitate was obtained therefrom by adding ethanol to the supernatant. This precipitate was dried and dissolved in 10 $\mu$l of distilled water to give a DNA sample.

(2) Pretreatment for Sequencing

Pretreatment for sequencing was performed with Auto-Read (TM) Sequencing Kit (Pharmacia).

Briefly, concentration of DNA for use as a template was adjusted to 5–10 ug in 32 $\mu$l of solution. Thirty two $\mu$l of the template DNA solution was transferred to 1.5 ml mini-tube (Eppendolf), and added thereto 8 $\mu$l of 2M NaOH aqueous solution, then mixed gently. After instant centrifugation, it was left at room temperature for 10 minutes.

Seven $\mu$l of 3M sodium acetate (pH 4.8) and 4 $\mu$l of distilled water were added thereto, then 120 $\mu$l of ethanol was also added and mixed, and the mixture was left for 15 minutes on dry ice. Then, DNA which was precipitated by centrifugation for 15 minutes was collected, and the supernatant was removed carefully therefrom. The precipitate obtained was washed with 70% ethanol and centrifuged for 10 minutes. Then, after the supernatant was removed carefully again, the precipitate was dried under the reduced pressure.

The precipitate was dissolved in 10 $\mu$l of distilled water, then 2 $\mu$l of fluorescent primer (0.42 A$_{260}$ unit/ml, 4–6 pmol), (Fluorescent Primer, M13 Universal Primer; 5'-Fluoroscein-d[CGACGTTGTAAAACGACGGCCAGT (SEQ ID NO: 8)]-3' (1.6 pmol/$\mu$l; 0.42 A$_{260}$ unit/ml); M13 Reverse Primer, 5'-Fluoroscein-d [CAGGAAACAGCTATGAC(SEQ ID NO: 9)]-3' (2.1 pmol/$\mu$l; 0.42 A$_{260}$ unit/ml)) and 2 $\mu$L of buffer for annealing were added thereto, and mixed gently.

After instant centrifugation, the mixture was heat-treated at 65° C. for 5 minutes and rapidly transferred to a circumstance of 37° C. and kept the temperature for 10 minutes. After keeping the temperature, it was left at room temperature for 10 minutes or more and centrifuged instantly. Then, a sample was prepared by adding 1 $\mu$l of a buffer for elongation and 3 $\mu$l of dimethyl sulfoxide thereto.

Four mini-tubes were identified with any of the marks of "A", "C", "G" or "T", and, according to each of the mark, respective 2.5 $\mu$l of A Mix (dissolved ddATP with dATP, dCTP, c$^7$dGTP and dTTP), C Mix (dissolved ddCTP with dATP, dCTP, c$^7$dGTP and dTTP), G Mix (dissolved ddGTP with dATP, dCTP, c$^7$dGTP and dTTP), and T Mix (dissolved ddTTP with dATP, dCTP, c$^7$dGTP and dTTP) were poured into each identified tube.

Each solution was preserved on ice until it was used, and was kept at 37° C. for one minute or more before use.

Two $\mu$l of diluted T7DNA polymerase (Pharmacia; 6–8 units/2 $\mu$l) was added to the DNA sample, and completely mixed through pipetting or mixing it gently. Immediately after the mixing was completed, the mixed solution was dispensed to 4.5 $\mu$l of the above four different solution respectively which had been thermal controlled. Fresh tip was used at each time of dispensation.

The solution was kept for 5 minutes at 37° C., then 5 $\mu$l of solution for terminating reaction was added to each reaction solution. Fresh tips were also used for dispensation on this dispensation step. Immediately after keeping the solution for 2–3 minutes at 90° C., it was cooled on ice. For electrophoresis, 4–6 $\mu$l of the solution per one lane was applied.

(3) Sequencing on Nucleotide Sequence

Sequencing on each nucleotide sequences of the probes disclosed in Example 1 and 2 having specificity to DNA from *Streptococcus pneumoniae* was performed using A.L.F. DNA Sequencer System (Pharmacia) under an electrophoresis condition of 45° C. for 6 hours.

Consequently, the entire nucleotide sequences of each of the probes: probe SP-22 (SEQ ID NO:1); probe SP-23 (SEQ ID NO:2); probe SP-25 (SEQ ID NO:3); probe SP-26 (SEQ ID NO:4); probe SP-5-15 (SEQ ID NO:5); probe SP-5-34 (SEQ ID NO:6); and probe SP-6-6 (SEQ ID NO:7) were clarified.

INDUSTRIAL APPLICABILITY

According to a probe of the present invention, bacteria for example, causative bacteria ingested into phagocytes can be directly detected without proliferating the bacteria, and can be identified rapidly and accurately. That is to say, according to diagnosis method using a probe of the present invention, identification of the bacteria can be accomplished with single specimen, then, the necessary time for diagnosis can be greatly reduced to about one to two days, while the conventional method (with low detection rate) required 3–4 days, and the detection efficacy is remarkably improved. Therefore, the present invention can provide breakthrough guide for the treatment of bacterial pneumonia, then enable the effective treatment in the early stage of the infectious diseases to the patient, as well as contribute to reduction in the mortality thereby.

Moreover, by clarifying the nucleotide sequences of the probes which specifically react with DNA from *Streptococcus pneumoniae*, one of the most closely related bacteria to attack of pneumonia among the causative bacteria of infectious diseases, artificial preparation of these probes could also be realized. Using the primers prepared by utilizing the information of the nucleotide sequences presently analyzed, DNA from the causative bacteria contained in the clinical specimen can be amplified by PCR technique, to serve rapid diagnosis of causative bacteria.

Further, by comparing the nucleotide sequences of genomic DNA from the clinical specimen with those analyzed in accordance with the present invention, rapid identification of the species of the causative bacteria of pneumonia can be carried out.

As stated above, the present invention provides a desired probe for diagnosing the infectious diseases, besides, excellent utilities are expected as a guide for preparing PCR primers and as a standard sequence suitable for the comparison and reference with genomic DNA from the clinical specimen. Additionally, the present invention exerts further outstanding effects, for example, of providing valuable clues for preparation and development of the other probes which specifically react with DNA from causative bacteria of the infectious diseases (causative bacteria of pneumonia).

Moreover, since the nucleotide sequences disclosed in the present application was obtained by random cloning of the genomic DNA from clinical isolates, thus, utilities of the nucleotide sequences disclosed in the present invention should be extended to the complementary sequences thereof.

Further, although it would be assumed that DNA obtained from the wild strain might contain a mutated portion, apparently from the disclosure of the examples above, such mutated DNA portion would never affect the utilities to be derived from the present invention such as the specificity of the probe of the present invention upon use for hybridization for diagnosis of the infectious diseases, and usage of the information on the nucleotide sequences disclosed in the present application to design the primer for PCR technique with the aim of a rapid diagnosis of the infectious diseases.

What is claimed is:

1. A purified nucleic acid probe for diagnosing infectious diseases caused by *Streptococcus pneumoniae,* the nucleic acid consisting of a nucleotide sequence selected from the group consisting of SEQ ID NOs: 1, 2, 5, 6, and 7, and nucleotide sequences fully complementary thereto.

2. A purified nucleic acid probe according to claim 1, the nucleic acid consisting of the nucleotide sequence set forth in SEQ ID NO: 1, or a nucleotide sequence fully complementary thereto.

3. A purified nucleic acid probe according to claim 1, the nucleic acid consisting of the nucleotide sequence set forth in SEQ ID NO: 2, or a nucleotide sequence fully complementary thereto.

4. A purified nucleic acid probe according to claim 1, the nucleic acid consisting of the nucleotide sequence set forth in SEQ ID NO: 5 or a nucleotide sequence fully complementary thereto.

5. A purified nucleic acid probe according to claim 1, the nucleic acid consisting of the nucleotide sequence set forth in SEQ ID NO: 6, or a nucleotide sequence fully complementary thereto.

6. A purified nucleic acid probe according to claim 1, the nucleic acid consisting of the nucleotide sequence set forth in SEQ ID NO: 7, or a nucleotide sequence fully complementary thereto.

7. A probe according to claim 1, said probe further comprising a detectable label.

8. A purified nucleic acid comprising of the nucleotide sequence set forth in SEQ ID NO: 4, or a nucleotide sequence fully complementary thereto, wherein said nucleic acid hybridizes to genomic DNA of *Streptococcus pneumoniae,* but fails to hybridize to genomic DNA of *Streptococcus agalactiae, Streptococcus anginosus, Streptococcus constellatus, Streptococcus equisimilis, Streptococcus faecium, Streptococcus faecalis, Streptococcus mitis, Streptococcus morbillorum, Streptococcus pyogenes, Streptococcus sanguis,* and *Streptococcus salivarius,* under the following hybridization and washing conditions:

hybridization overnight at 42° C. in a hybridization solution comprising 45% formamide and 5×SSC; and washing twice for 20 minutes at 55° C., in a washing solution comprising 0.1×SSC and 0.1% SDS.

9. A purified polynucleotide consisting of a nucleotide sequence selected from the group consisting of SEQ ID NO: 1, SEQ ID NO: 2, SEQ ID NO: 4, SEQ ID NO: 5, SEQ ID NO: 6, SEQ ID NO: 7, and nucleotide sequences fully complementary thereto, wherein said polynucleotide hybridizes to genomic DNA of *Streptococcus pneumoniae,* but fails to hybridize to genomic DNA of *Streptococcus agalactiae, Streptococcus anginosus, Streptococcus constellatus, Streptococcus equisimilis, Streptococcus faecium, Streptococcus faecalis, Streptococcus mitis, Streptococcus morbillorum, Streptococcus pyogenes, Streptococcus sanguis,* and *Streptococcus salivarius,* under the following hybridization and washing conditions:

hybridization overnight at 42° C. in a hybridization solution comprising 45% formamide and 5×SSC; and washing twice for 20 minutes at 55° C., in a washing solution comprising 0.1×SSC and 0.1% SDS.

10. A probe for the diagnosis of infectious disease caused by *Streptococcus pneumoniae,* consisting of the purified polynucleotide according to claim 9, said probe further comprising a detectable label.

11. A vector containing a nucleic acid insert, wherein the nucleic acid insert consists of a nucleic acid, nucleic acid probe, or polynucleotide according to any one of claims 1, 2, 3, 4, 5, 6, 8, or 9.

12. A purified nucleic acid probe for diagnosing infectious diseases caused by *Streptococcus pneumoniae,* wherein the nucleotide sequence of said nucleic acid consists of a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7, and nucleotide sequences fully complementary thereto.

13. The nucleic acid probe according to claim 12, wherein the probe further includes a detectable label attached to the nucleic acid.

14. The nucleic acid probe according to claim 12, wherein the nucleic acid contains at least one radioisotope.

15. A vector containing a nucleic acid insert, wherein the nucleic acid insert consists of a nucleotide sequence selected from the group consisting of SEQ ID NOs: 1, 2, 5, 6, and 7, and nucleotide sequences fully complementary thereto.

* * * * *